United States Patent
Richard et al.

(10) Patent No.: US 9,347,876 B2
(45) Date of Patent: May 24, 2016

(54) INFRARED OPTICAL SENSOR INCORPORATING A TRANSMISSION MEASURING CELL

(71) Applicants: CONTINENTAL AUTOMOTIVE FRANCE, Toulouse (FR); CONTINENTAL AUTOMOTIVE GmbH, Hannover (DE)

(72) Inventors: Herve Richard, Toulouse (FR); Antoine Pianu, Pompignan (FR)

(73) Assignees: CONTINENTAL AUTOMOTIVE FRANCE, Toulouse (FR); CONTINENTAL AUTOMOTIVE GMBH, Hannover (DE)

( * ) Notice: Subject to any disclaimer, the term of this patent is extended or adjusted under 35 U.S.C. 154(b) by 121 days.

(21) Appl. No.: 14/168,789

(22) Filed: Jan. 30, 2014

(65) Prior Publication Data

US 2014/0211197 A1    Jul. 31, 2014

(30) Foreign Application Priority Data

Jan. 31, 2013 (FR) ..................... 13 50855

(51) Int. Cl.
*G01J 5/02* (2006.01)
*G01N 21/3504* (2014.01)
(Continued)

(52) U.S. Cl.
CPC ............ *G01N 21/3504* (2013.01); *G01N 21/05* (2013.01); *G01N 21/3577* (2013.01); *G01N 21/85* (2013.01); *G01N 21/15* (2013.01);
(Continued)

(58) Field of Classification Search
CPC ... G01N 21/3577; G01N 21/05; G01N 21/85; G01N 21/3504; G01N 33/22

USPC ............................................ 250/343; 356/51
See application file for complete search history.

(56) References Cited

U.S. PATENT DOCUMENTS 4,835,389 A * 5/1989 Doyle ........................... 250/343
6,842,234 B2    1/2005 Kong et al.
(Continued)

FOREIGN PATENT DOCUMENTS

| DE | 28 38 396 A1 | 3/1980 |
| DE | 35 03 626 A1 | 8/1986 |
| DE | 40 14 739 A1 | 11/1991 |
| DE | 10 2006 041274 A1 | 3/2008 |
| WO | 2011/127551 A1 | 10/2011 |

OTHER PUBLICATIONS

French Search Report, dated Sep. 26, 2013, from corresponding French application.

*Primary Examiner* — David Porta
*Assistant Examiner* — Abra Fein
(74) *Attorney, Agent, or Firm* — Young & Thompson

(57) ABSTRACT

Disclosed is an infrared optical sensor for the continuous analysis of a liquid flowing in a pipe. The sensor includes, in a housing, a central section of duct through which the liquid to be analyzed flows, and a spectral analysis device using a light beam, including an infrared source which emits a signal which is received by a receiving device having passed through the liquid, an optical component which allows the light beam to pass through the liquid, and a support plate which carries the infrared source and the receiving device. The liquid to be analyzed circulates through a loop formed by walls in the form of an arch of the optical component and by a projection of the housing in the optical component. A sealing gasket is compressed between the optical component and the housing, in order to prevent any diffusion of liquid on the interior of the housing.

14 Claims, 3 Drawing Sheets

(51) Int. Cl.
  *G01N 21/05*   (2006.01)
  *G01N 21/3577*  (2014.01)
  *G01N 21/85*   (2006.01)
  *G01N 21/15*    (2006.01)
  *G01N 21/359*   (2014.01)
  *G01N 33/28*    (2006.01)

(52) U.S. Cl.
  CPC .......... *G01N21/359* (2013.01); *G01N 33/2835* (2013.01); *G01N 2021/8557* (2013.01); *G01N 2201/021* (2013.01); *G01N 2201/0228* (2013.01); *G01N 2201/0636* (2013.01)

(56) References Cited

U.S. PATENT DOCUMENTS

| | | | |
|---|---|---|---|
| 7,242,001 B1 * | 7/2007 | Hedges et al. | 250/343 |
| 7,339,657 B2 | 3/2008 | Coates | |
| 7,605,361 B2 * | 10/2009 | Uchida et al. | 250/227.25 |
| 2005/0040335 A1 * | 2/2005 | Hauschild et al. | 250/339.13 |
| 2007/0201028 A1 * | 8/2007 | Myers et al. | 356/338 |
| 2009/0064803 A1 * | 3/2009 | Pettit et al. | 73/866.5 |

\* cited by examiner

INFRARED OPTICAL SENSOR INCORPORATING A TRANSMISSION MEASURING CELL

FIELD OF THE INVENTION

The invention relates to an infrared optical sensor incorporating a transmission measuring cell for the real-time analysis of liquids, wherein said sensor can specifically be used for the continuous analysis of a liquid flowing in a pipe.

In its main, but not exclusive application, the invention relates to the monitoring of the quality and composition of fuel in vehicles, by means of on-board sensors in said vehicles. This monitoring has become essential in response to the expanding use of biodiesel from various sources and of varying compositions.

If this monitoring is carried out in real time, it will allow the control system of the vehicle to adjust various engine setting parameters in the interests of improving the efficiency of combustion, e.g. the quantity of fuel injected, ignition timing, the inlet pressure or emission control settings.

The composition of fuels may be monitored at the fuel station pump, where quality must be maintained at a constant level, given the wide selection of petroleum-based fuels or biofuels containing variable percentages of ethanol. A simple means of establishing this composition involves the use of sensors installed in the fuel tank, or between the fuel tank and the engine, in order to allow the electronic control system of the vehicle to adjust the engine setting parameters. The infrared spectrum is now recognized as relevant for the optical analysis of the characteristics of fuels and lubricants, including the octane index, oxidation and dilution.

BACKGROUND OF THE INVENTION

Many types of sensors are available for the analysis of fluids. However, only certain sensors are designed to operate in real time, which is an essential prerequisite for the management of the combustion efficiency of an engine. Patent document U.S. Pat. No. 6,842,234 describes a sensor of this type comprising a two-strand optical fiber, one end of which is inserted as a probe into the liquid to be analyzed, and the other end of which is connected to a signal processing device.

The signal processing device generates an infrared optical signal in the first strand of said fiber, which terminates in the liquid opposite a reflector. This reflector reflects the optical signal towards the second strand of fiber. Accordingly, at the other end of the fiber, the processing device analyzes an optical signal which has passed through the probe which is immersed in the liquid to be analyzed. The temperature and composition of the liquid to be analyzed will modify the return optical signal to the processing device.

In order to ensure that the optical signal is fully reflected within the fiber-optic strands, two conditions must be fulfilled: the refractive index of the fiber-optic glass must be higher than that of the liquid through which the fiber passes, and the radius of curvature of the optical fiber must be sufficiently large. Accordingly, a sensor of this type is bulky in construction and costly.

Examples of less bulky and less expensive sensors are described in patent document U.S. Pat. No. 7,339,657. This document describes sensors based upon the principle of reflective infrared spectroscopy. According to this principle, an infrared ray is emitted by light-emitting diodes (LEDs) on the interior of an optical structure of the multi-faceted crystal type, the external facets of which are in contact with the liquid to be analyzed, and the internal volume of which accommodates the passage of the light ray.

This faceted structure ensures that there will be at least two reflections of the light ray in its internal volume. The outward path of the light ray from the LED and the return path of this ray to its point of analysis run in parallel, but in opposite directions. This outward/return path of the ray allows the infrared emitter and the analytical device to be installed on a single circuit board. Reflections of the infrared ray from the internal walls of the optical structure, upon the analysis of the return ray, allow the deduction of various physical or chemical parameters of the analyzed liquid on the other side of the optical structure. The structure of these sensors—incorporating LEDs, a single circuit board and a limited volume—is consistent with relatively low production costs and the on-board installation of said sensors in a vehicle.

However, the optical structure creates a projection on the interior of the volume of liquid to be analyzed. As a result of this projection, the circulating liquid forms a retention pocket ahead of the optical structure (in the direction of flow), such that residues (soot, impurities, etc.) will accumulate in said retention pocket. Moreover, the crystals used are both expensive and fragile.

The invention is intended to overcome these drawbacks by the application of transmission infrared spectroscopy and the use of a device for the continuous analysis of the total volume of fuel passing through an unobstructed duct, thereby permitting the analysis of the fuel flowing in said duct with no formation of a retention pocket in the liquid, and no resulting stagnation of residues.

SUMMARY OF THE INVENTION

More specifically, the subject of the present invention is an optical sensor for the analysis of liquid, wherein the sensor comprises, in a housing, a central section of duct through which the liquid flows, and a spectral analysis device using a light beam in a wavelength band. In this device, the beam is emitted by an infrared source and received by a receiving device, having passed through the liquid to be analyzed via an optical component. A support plate arranged on a base carries the infrared source and the receiving device. In this sensor, the liquid to be analyzed flows through a loop in the central section of duct enclosed by walls of the optical component, which form an arch, and the housing, which forms a projection in said arch. A sealing gasket is compressed between the optical component and the housing, in order to prevent any diffusion of liquid into the interior of the housing.

The looped configuration of the duct for the liquid circulation within the optical component permits the analysis of liquid by transmission spectroscopy, without creating any obstacle in the liquid path and, accordingly, with no formation of a stagnant liquid pocket and the resulting accumulation of deposits, as in the case of sensors employing reflection spectroscopy.

According to the following specific advantageous features:
the optical component incorporates at least one combination comprised of a first and second reflective wall, which are inclined in relation to the optical beam, thus forming an outward/return optical path on the support plate between the infrared source and the receiving device;
the first reflective wall and the second reflective wall are configured as plane or aspherical concave surfaces;
the light beam is divergent in the direction of the first reflective wall, which is configured as a concave wall, such that the beam substantially passes through the liquid to be analyzed, which flows in the loop formed by the central section of the duct, and is focused on the second reflective wall before reaching the receiving device;

at least one of the reflective walls is comprised of a reflector which is secured to the optical component;

in service, the optical component forms a twin arch, whereby a first arch is formed in the plane of propagation of the light beam, and a second arch is formed in a plane which is perpendicular to said plane of propagation;

the arches and the projection of the housing form the loop in the central section of duct at the core of the optical component which accommodates the liquid to be analyzed;

the wavelength band lies in the near-infrared spectrum;

the infrared source is a light-emitting diode (or "LED");

means of attachment are provided for the secure fixing of the support plate to the housing, in order to permit the adjustable compression of the gasket.

The invention also relates to a method for the analysis of liquid, in which the above-mentioned sensor is used. This method involves the following:

a first step, in which the liquid to be analyzed is circulated in the loop of the sensor described above;

a second step, in which the infrared source of the sensor for the emission of a divergent beam is turned on;

a third step, in which the light beam is oriented in the optical component towards the first reflective wall, which renders said beam convergent, and is then routed via the loop, whereafter it undergoes a second reflection on the second reflective wall, and finally towards the receiving device on the support plate.

According to one variant of this method, the light beam is dispersed such that the full beam does not reach the receiving device; in this case, the base is configured for at least the partial reception of said dispersed beam. This reception by the base supplements reception by the receiving device, thereby increasing the optical efficiency of measurement.

BRIEF DESCRIPTION OF THE DRAWINGS

Further information, characteristics and advantages of the present invention will become evident from the following description, which is not provided by way of limitation, with reference to the attached figures in which, respectively.

DETAILED DESCRIPTION OF THE INVENTION

Figure 1:
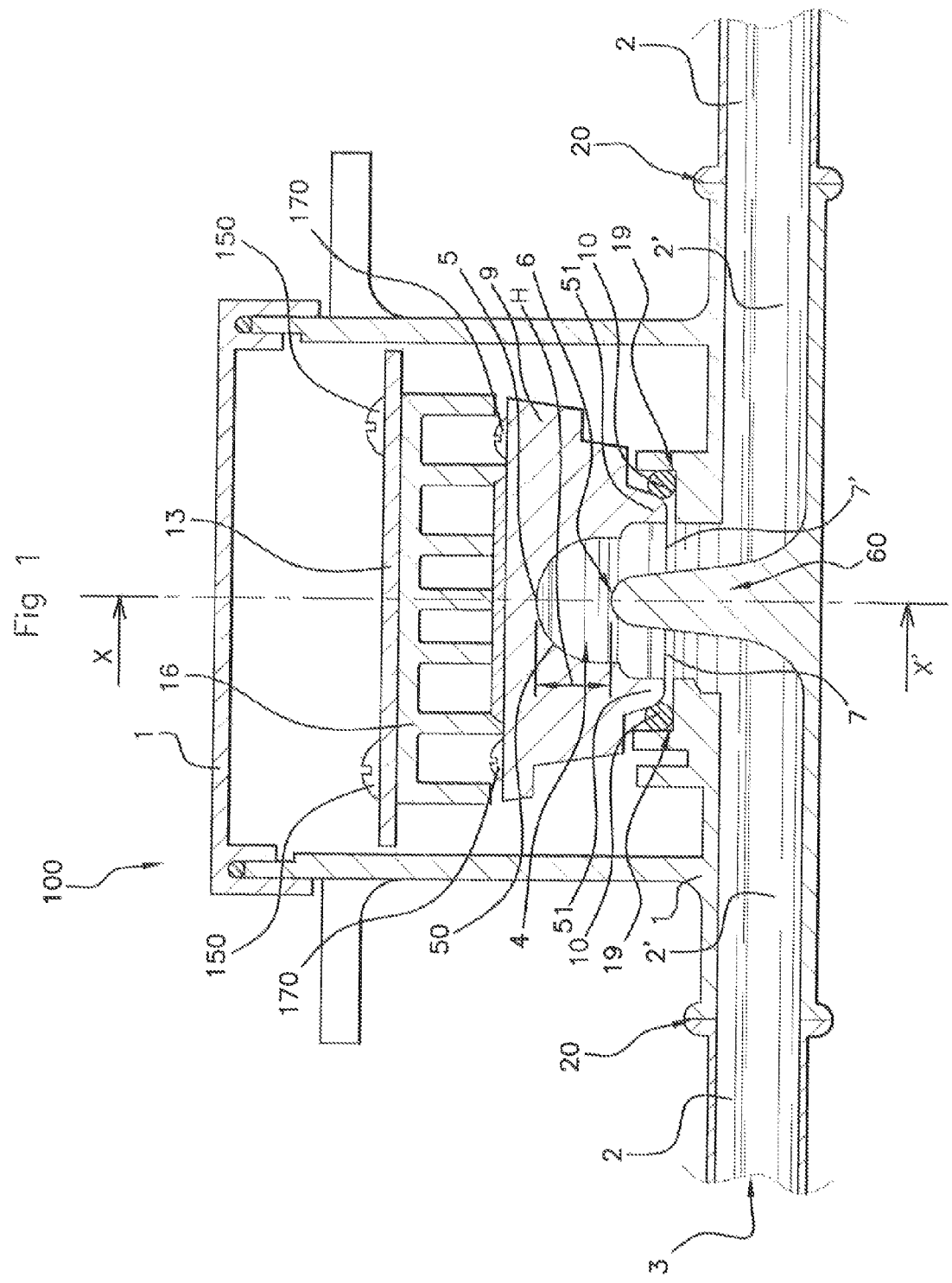
FIG. 1 shows a cross-sectional view of an example of an infrared optical sensor according to the invention, in a plane of circulation of the fluid to be analyzed.

With reference to the view shown in FIG. 1, an example of embodiment of the infrared optical sensor 100 is represented in cross-section in a plane of circulation of the fluid 3 to be analyzed. This fluid 3, a fuel in the example illustrated, flows in a duct comprised of an external duct 2 to the sensor 3, connected by fasteners 20 to a central section of duct 2' formed within the sensor 100. Said sensor 100 is provided with a housing 1 of a plastic material which encloses all the dedicated components for the analysis of the fuel 3 as detailed hereinafter. An optical analysis of said fuel 3 will be executed on the basis of an infrared light beam which passes through this central section of duct 2'. This central section of duct 2' is provided with a loop 4 comprised of a vaulted profile 5, an arch 50 in its upper section formed in a glass optical component 9, and a lower surface 6 of a projection 60 of the housing 1 in said optical component 9. The feet 51 of the arch 50 terminate at levels 7 and 7' on either side of the projection 60.

FIG. 1 also shows an equipment support plate 13 (see FIG. 2) resting on a base 16 and secured to the optical component 9 by means of screws (only the heads 150 of said screws are visible in FIG. 1). An O-ring 10 secures the feet 51 of the optical component against a circular corner angle 19 of the housing 1, in order to prevent any leakage of fuel into the housing 1 from the central section of duct 2'.

Further screws (only the heads of which 170 are visible on FIG. 1) are provided for the close attachment of the support plate 13 of the housing 1, thereby compressing the O-ring 10 and ensuring the leak-tightness of the central section of duct 2'.

The light beam traverses the central section of duct 2' over substantially the full upper height H of said central section of duct 2', i.e. between the apexes of the vaulted profile 5 and of the projection 60. This permits the execution of transmission spectroscopy, as described hereinafter.

Figure 2:
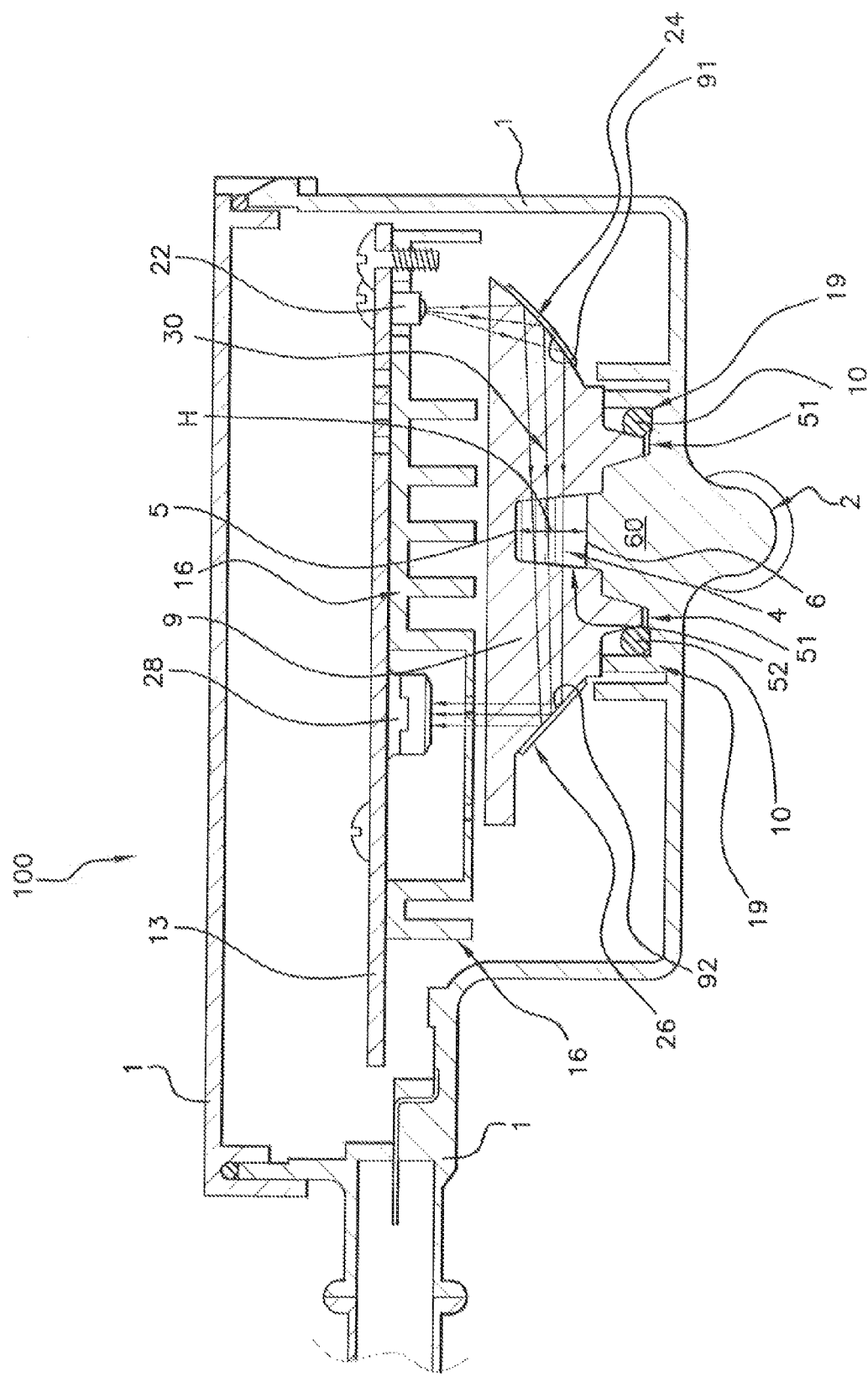
FIG. 2 shows a cross-sectional plane view at X'X in FIG. 1 of the infrared optical sensor according to the invention, in the plane of propagation of light rays which is perpendicular to the plane of circulation of the fluid.

FIG. 2 shows a cross-sectional view of the infrared optical sensor 100 in a plane of propagation of the light beam 30 according to the invention, perpendicularly to the cross-sectional view shown in FIG. 1 at plane X'X. The loop 4 of the glass optical component 9 is provided with an arch 52, perpendicular to the arch 50 shown in FIG. 1, whereby these two arches have the same vaulted profile 5. The central section of duct 2' is represented at the level of the loop 4, as defined by its upper height H. The outline of the central section of duct 2' is then formed by the glass optical component 9 of the sensor 100 on all its faces, excepting the lower face, which is formed by the face 6 of the projection 60 of the plastic material housing 1. FIG. 2 also shows the outline of the external duct 2, which coincides with the outline of the central section of duct 2', outside the optical component 9.

The O-ring 10 is compressed into the corner angle 19 of the housing 1, thereby securing the feet 51 of the optical component 9.

This cross-section illustrates the path of the light beam 30 traversing the fuel to be analyzed. It traverses said fuel over substantially the full height H between the apexes of the vaulted profile 5 and of the face 6. Said light beam 30 is emitted by the infrared source 22 secured to the support plate 13 and equipped with an LED for the emission of infrared light of wavelength ranging from 1500 nm to 2000 nm in the example considered.

The light beam 30 then traverses the optical component 9 over its full width, describing a path which, on average, generates two right-angled reflections from the fully-inclined faces 91 and 92 of the optical component 9, thereby returning the beam 30 to the receiving device 28 secured to the support plate 13. Reflections are generated by a first reflector 24, secured to the face 91 of the optical component 9, and by a second reflector 26, secured to the face 92 of the optical component 9.

The first reflector 24 is an aspherical concave reflector, and the second reflector is a plane reflector 26. The divergent light beam 30 is emitted towards the first reflector 24, thereby allowing the beam 30 to traverse the central section of duct 2' over virtually the entire upper height H of the loop 4 in the central section of duct 2', before converging towards the second reflector 26 and then being directed towards the receiving device 28.

Figure 3:
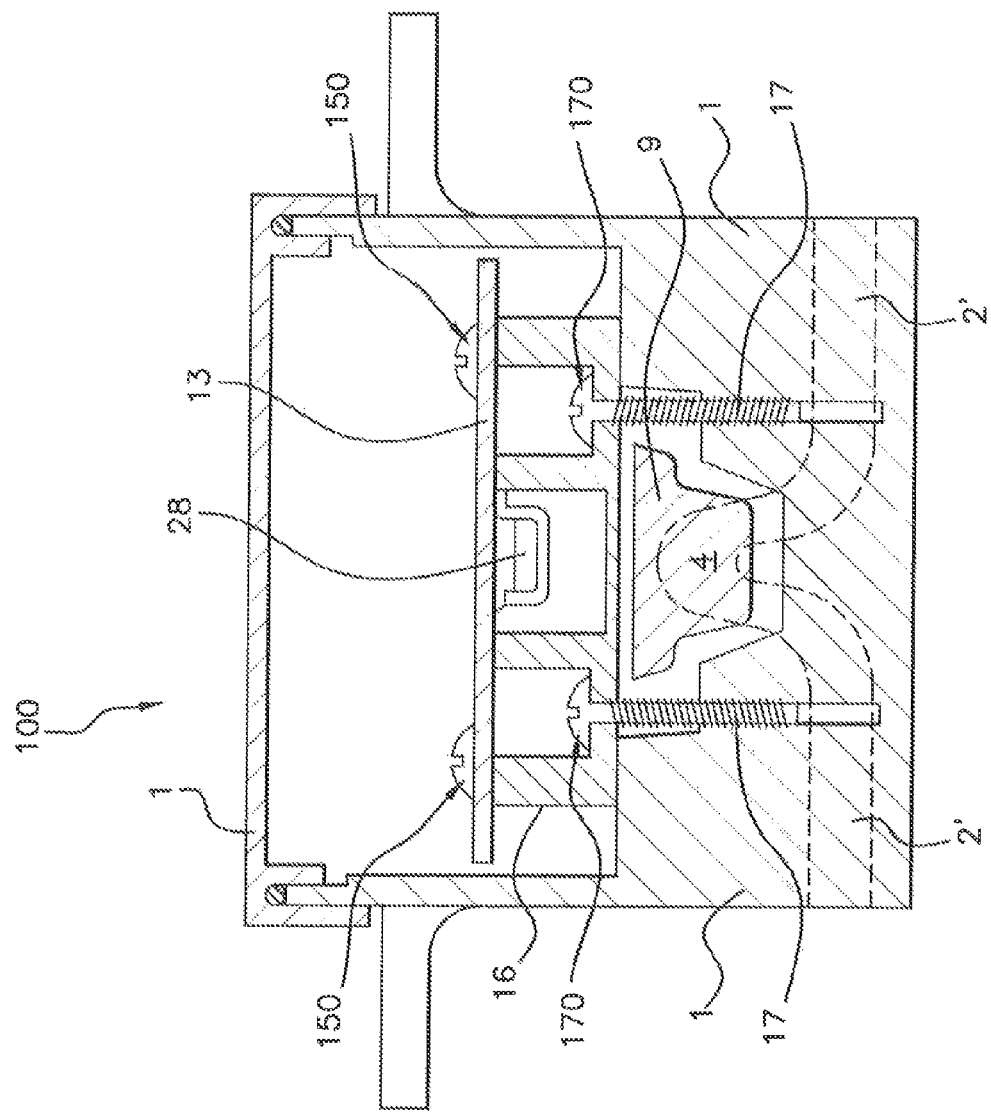
FIG. 3 shows a cross-sectional view of the infrared optical sensor according to the invention, in the plane of the screws between the optical component and the compression housing.

FIG. 3 shows a cross-sectional view of the example of the sensor 100 according to the invention, in the plane of the screws 17 for the attachment of the optical component 9 against the housing 1 via the attachment of the base 16 of the support plate 13 to the housing 1. The screws 17 compress the O-ring 10 (FIG. 1 or 2) which forms a seal between the optical component 9 and the housing 1, thereby ensuring the leak-tightness thereof. The remaining screws, only the heads 150 of which are visible, lie in a different cross-sectional plane. These screws secure the support plate 13 to the optical component 9. In addition, on FIG. 3, dashed lines represent the central section of duct 2' forming the loop 4 in a plane which is parallel to the plane of the figure, together with the receiving device 28 of the sensor 100.

The invention is not restricted to the examples of embodiment described and represented. Apart from fuels, many liquids are suitable for continuous analysis by transmission using an optical sensor of this type, provided that the liquid concerned has a transmittance factor other than zero.

This type of sensor may be installed in the fuel supply line of an engine, at the outlet of a fuel tank, or in any circuit in which the monitoring of the quality of a fluid is required.

The light beam may also be propagated in a perpendicular or parallel plane to the plane of circulation of the fluid to be analyzed.

In respect of the aperture angle of the light beam upon emission, this aperture may be set for divergence or convergence, according to the curvature(s) of the reflective walls.

Moreover, multiple wavelengths may be applied simultaneously, in the interests of the enrichment of results obtained from analyses conducted using a light beam received after its passage through a liquid.

Wavelengths other than those in the near-infrared spectrum may be used, e.g. mid-infrared or far-infrared. Measurement may be effected using a single wavelength, or within a range of wavelengths.

The loop formed by the duct on the interior of the sensor may also be configured as an arch which is oriented in different directions in relation to gravity: not only downward, but also upward or lateral orientation is possible. The pressure of the fluid in circulation prevents any deposition of impurities in the loop.

The invention claimed is:

1. An optical sensor for the analysis of a liquid, the optical sensor (100) comprising:
a housing (1);
a duct (2') having a central section configured to permit the liquid to flow; and
a spectral analysis device, comprising an infrared source (22) that emits a light beam (30) in an infrared wavelength band, and a receiving device (28) that receives the light beam (30), the light beam arranged to pass through the liquid before being received by the receiving device, the spectral analysis device further comprising a base (16), an optical component (9) that analyzes the light beam, and a support plate (13), arranged on the base (16), which carries the infrared source (22) and the receiving device (28),
wherein the liquid is caused to flow through a loop (4) in the central section of the duct (2') enclosed by walls of the optical component (9) that forms twin arches (50, 52),
wherein the housing (1) forms a projection (60) in said twin arches,
wherein a sealing gasket (10) is compressed between the optical component (9) and the housing (1) such to prevent any diffusion of the liquid on an interior of the housing (1), and
wherein a first arch (52) of the twin arches is formed in a plane of propagation of the light beam (30), and a second arch (50) of the twin arches is formed in a plane perpendicular to said plane of propagation of the light beam (30).

2. The optical sensor for the analysis of a liquid as claimed in claim 1, wherein the optical component (9) incorporates at least one combination comprised of a first (91) reflective wall and a second (92) reflective wall, said first and second reflective walls being inclined in relation to the optical beam (30) to form an outward/return optical path on the support plate (13) between the infrared source (22) and the receiving device (28).

3. The optical sensor for the analysis of a liquid as claimed in claim 2, wherein the first reflective wall (91) and the second reflective wall (92) are configured as planar or aspherical concave surfaces.

4. The optical sensor for the analysis of a liquid as claimed in claim 3, wherein the light beam (30) is divergent in a direction of the first reflective wall (91), said first reflective wall (91) configured as a concave wall, such that the light beam (30) passes through the liquid that flows in the loop (4) and is focused on the second reflective wall (92) before reaching the receiving device (28).

5. The optical sensor for the analysis of a liquid as claimed in claim 3, wherein at least one of the first and second reflective walls is comprised of a reflector (24, 26) secured to the optical component (9).

6. The optical sensor for the analysis of a liquid as claimed in claim 2, wherein the light beam (30) is divergent in a direction of the first reflective wall (91), said first reflective wall (91) configured as a concave wall, such that the light beam (30) passes through the liquid that flows in the loop (4) and is focused on the second reflective wall (92) before reaching the receiving device (28).

7. The optical sensor for the analysis of a liquid as claimed in claim 6, wherein at least one of the first and second reflective walls is comprised of a reflector (24, 26) secured to the optical component (9).

8. The optical sensor for the analysis of a liquid as claimed in claim 2, wherein at least one of the first and second reflective walls is comprised of a reflector (24, 26) secured to the optical component (9).

9. The optical sensor for the analysis of a liquid as claimed in claim 1, wherein the twin arches (50, 52) and the projection (60) of the housing (1) form the loop (4) in the central section of duct (2') at a core of the optical component (9) which accommodates the liquid.

10. The optical sensor for the analysis of a liquid as claimed in claim 1, wherein the wavelength band is in the near-infrared spectrum.

11. The optical sensor for the analysis of a liquid as claimed in claim 1, wherein the infrared source (22) is a light-emitting diode.

12. The optical sensor for the analysis of a liquid as claimed in claim 1, wherein means of attachment (15, 17) are provided for a secure fixing of the support plate (13) to the housing (1) that enables adjustable compression of the gasket (10).

13. A method for the analysis of a liquid, comprising:
providing an optical sensor (100), that comprises
a housing (1),
a duct (2') having a central section configured to permit the liquid to flow, and
a spectral analysis device, comprising an infrared source (22) that emits a light beam (30) in an infrared wavelength band, and a receiving device (28) that receives the light beam (30), the light beam arranged to pass through the liquid before being received by the receiving device, the spectral analysis device further comprising a base (16), an optical component (9) that analyzes the light beam, and a support plate (13), arranged on the base (16), which carries the infrared source (22) and the receiving device (28), wherein the liquid is caused to flow through a loop (4) in the central section of the duct (2') enclosed by walls of the optical component (9) that forms twin arches (50, 52), wherein the housing (1) forms a projection (60) in said twin arches, wherein a sealing gasket (10) is compressed between the optical component (9) and the housing (1) such to prevent any diffusion of the liquid on an interior of the housing (1), and wherein a first arch (52) of the twin arches is formed in a plane of propagation of the light beam (30), and a second arch (50) of the twin arches is formed in a plane perpendicular to said plane of propagation of the light beam (30);

circulating the liquid in the loop (4) of the central section of duct (2') of the sensor;

turning on the infrared source (22) of the sensor to emit a divergent beam (30); and orienting the light beam (30) in the optical component (9) towards a first reflective wall (91) of the optical component to render the light beam convergent, and then routing the beam via the loop (4), whereafter the light beam undergoes a second reflection on a second reflective wall (92) of the optical component, and finally is routed towards the receiving device (28) on the support plate (13).

14. The analysis method as claimed in claim 13, wherein the light beam (30) is dispersed such that a full beam of the light beam does not reach the receiving device (28), and the base (16) is configured for at least partial reception of said dispersed beam, such that the reception by the base (16) of said dispersed beam supplements reception by the receiving device (28).

* * * * *